United States Patent [19]
Ward et al.

[11] Patent Number: 5,754,121
[45] Date of Patent: May 19, 1998

[54] JOINT MONITOR

[76] Inventors: Francisco A. Ward, 4604 Mews Dr., Owings Mills, Md. 21117; Michael S. Bullinger, 14610 Bowie Rd., Laurel, Md. 20708

[21] Appl. No.: 706,789

[22] Filed: Sep. 3, 1996

[51] Int. Cl.⁶ ............................................. G08B 23/00
[52] U.S. Cl. ................... 340/870.09; 340/573; 128/782; 128/774
[58] Field of Search ........................... 340/870.09, 573, 340/870.05; 128/782, 774, 781

[56] References Cited

U.S. PATENT DOCUMENTS

| | | | |
|---|---|---|---|
| 3,020,639 | 2/1962 | Karpovich et al. | 33/1 |
| 3,258,007 | 6/1966 | Karpovich et al. | 128/2 |
| 4,436,099 | 3/1984 | Raftopoulos | 128/782 |
| 4,534,364 | 8/1985 | Lamoreux | 128/774 |
| 4,665,928 | 5/1987 | Linial et al. | 128/782 |
| 4,969,471 | 11/1990 | Daniel et al. | 128/774 |
| 5,078,152 | 1/1992 | Bond et al. | 128/774 |
| 5,216,817 | 6/1993 | Misevich et al. | 33/515 |
| 5,220,308 | 6/1993 | Batzdorff et al. | 340/573 |
| 5,230,623 | 7/1993 | Guthrie et al. | 433/72 |
| 5,263,492 | 11/1993 | Voyce | 128/782 |
| 5,368,546 | 11/1994 | Stark et al. | 601/34 |
| 5,402,107 | 3/1995 | Rencavage | 340/573 |

Primary Examiner—Jeffery Hofsass
Assistant Examiner—Albert K. Wong
Attorney, Agent, or Firm—Leonard Bloom

[57] ABSTRACT

A dual-plane joint monitor has a pair of arms for releasable attachment to body joint members and a gimbal assembly connecting the arms for their relative rotation in two perpendicular planes. Two potentiometers generate signals indicative of an angular motion of the arms. A miniaturized electronic module, worn by a patient, is pre-programmed from a remote computer (an allowed range of motion is pre-set), reads and processes signals from the potentiometers and determines whether the allowed range of motion is exceeded. The data stored in the electronic module are transmitted periodically to the remote computer for further analysis. If needed, the physician re-programs the electronic module from the computer at a medical facility while the patient is at home, or at another remote location.

17 Claims, 10 Drawing Sheets

JOINT MONITOR

FIELD OF THE INVENTION

The present invention relates to a joint monitor for controlling and facilitating a rehabilitation process after a surgery on a body joint, and more particularly, to a multiplane joint monitor capable of two-way remote communication with a medical facility.

BACKGROUND OF THE INVENTION

It is known that after orthoplastic surgery of body joints, such as hip or knee, a physician establishes for a patient certain motion precautions. As part of the rehabilitation process, a variety of monitoring and post-operative devices are used, which are intended to prevent subsequent dislocations which, in turn, would require reconstructive surgery or the use of a cast to immobilize the patient.

These devices, basically, provide a warning signal as a warning to the patient that he (or she) has exceeded the present limits of movement.

For example, U.S. Pat. No. 5,402,107 discloses an apparatus attached to a body part for detection when the body part attitude exceeds a specific attitude range. For every such attitude violation, the apparatus sounds a buzzer and increments a displayed counter value that indicates the total number of such attitude violations.

For decades, researchers and therapists have been actively involved in designing improved methods and approaches for measuring the amount of angular rotation between two human body portions connected to the common joint, which is the basics for most monitoring and post-operative devices for body joints.

Typically, these devices include two extensions, pivotally connected to each other each for attachment to a body part, and a device connected between the two extensions for measuring the angle therebetween and for producing a certain output corresponding to the angle.

For example, U.S. Pat. Nos. 3,020,639, 3,258,007, and 4,436,099 describe apparatuses for measuring angles of body joints during various physical movements and producing recording of electrical signals, the magnitude of which is proportional to the measured angle. A potentiometer is employed for measuring the angular position between the two body portions and for generating electric signals which are further supplied to a counter or display circuit for being displayed in angular degrees.

U.S. Pat. No. 5,263,492 describes a recording goniometer which measures and records the flexibility or extent of limb movement about the joint by means of the scribing element which records concentric arc segments on a replaceable recordation paper which readily indicates comparative subtended arc segments as a determination of healing process.

A need has developed in the art for a measuring instrument able to measure the range of motion of the various joints of the body to within an error of 1% or less. In response to this need, computerized systems have been designed and used.

For instance, a device, disclosed in U.S. Pat. No. 4,665,928, includes a newly designed electronic goniometer consisting of a sensitive gear system (optionally used in conjunction with an infrared light system) to sense movement, react to those movements and measure the movements with increased accuracy. The electronic goniometer outputs voltages interpretable by the micro-computer which are indicative of a rotation of the goniometer with respect to an original vertical position. A plurality of such electronic goniometers can be attached to joints of the body by an elastic band so as to simultaneously determine the range of motion of a plurality of body joints with respect to one another, thereby monitoring various exercises over the whole body.

A computerized exercise system for diagnosis and/or training of proprioceptor feedback capabilities in a muscle and joint system of a human patient is described in U.S. Pat. No. 5,078,158. The system uses a patient attachment device and a means for controlling parameters of an exercise movement in response to a control signal derived from one or more measured exercise parameters.

U.S. Pat. No. 5,368,546 describes a computerized orthopedic restraining device which has an ambulatory housing including a pair of end distal members and an elongated restraining bar equipped with a stress sensing mechanism for restraining movement of the end distal members relative to one another. A control unit is provided for indicating sensed stress based upon outputs from the stress sensing mechanism. The stress sensing mechanism can be adjusted to different degrees of flexion or extension.

Disadvantageously, despite that all of the above devices have certain utility for their intended purposes, none of them nevertheless allows monitoring of two or more planes of a joint motion.

U.S. Pat. No. 5,220,308 describes a joint excursion monitor device which, when strapped onto a patient's leg, can monitor preset limits in two generally perpendicular planes of the joint motion.

In the event, that the preset limit is reached, the device generates an alarming signal.

The device includes an upper bar and a lower bar hinged to each other by the ball-type joint. The upper bar is strapped to the patient's leg. Mounted on the upper bar is the two-part plastic stator, which accommodates a metallic rotor mounted on the lower bar. When the rotor rotates within the stator, it makes contact with a spring-loaded ball mounted in the stator. The metallic rotor has a non-metallic insert which interrupts the circuit when reaches the ball contact. In this event, the excursion monitor signal is initiated. To preset the excursion limit, the stator is pre-adjusted by manually rotating the stator with respect to the upper bar and clamping it in place with the clamp screw.

Mounted on the rotor is a plunger contact. When the leg adduction reaches the preset limit, the plunger contact makes contact with the adduction signal disk, thus completing a circuit and initiating an alarm signal. The adduction limit is preset by manual adjustment of the angle between the mounting plate and the lower bar.

A signal box which is worn on the patient's belt and is connected to the stator-rotor contacts by a cable, includes a signal generator, an excursion counter, a limit counter, a selector switch, a power supply, an internal computer, a transmitting means for transmitting data to any external device suitable to perform all counting and performing functions.

Disadvantageously, the stator-rotor system of the '308 device is somewhat complicated, requires a troublesome manual mechanical pre-adjustment and re-adjustment of limits that may cause undesirable errors and subsequent unwanted dislocation which must be avoided.

As a major disadvantage, none of the prior art joints monitoring devices allows continuous monitoring and controlling of the body joint while the patient is out of the medical facility.

SUMMARY OF THE INVENTION

It is, therefore, an object of the present invention to provide a multi-plane joint monitor easily re-adjustable for motion precaution and alarming purposes, able of high accuracy measure of motion of various body joints.

It is another object of the present invention to provide a multi-plane joint monitor having the ability to monitor the motion range of a body joint, to store, process and output data in a desired format, and to be re-programmed and re-adjusted from a remote location such that a patient does not need to present at a medical facility for these purposes.

It is still an object of the present invention to provide a multi-plane joint monitor employing a pair of conventional potentiometers, each for sensing the joint motion in one of the motion planes and generating signals indicative of the measured motion.

It is yet another object of the present invention to provide a simple, yet effective mechanism connecting the upper and lower arms of the joint monitor allowing two-axis motion of the arms relative to each other.

It is still an object of the present invention to provide a method for manipulating the multi-plane joint monitor by means of a software from a remote computer.

It is a further object of the present invention to provide a method for monitoring a body joint motion in at least two planes, and to process the obtained data for rehabilitation, training, researching, etc., purposes.

The present invention finds particular utility for monitoring hip or knee joints, but also can be implemented for other body joints.

In accordance with the teachings of the present invention, a joint monitor comprises first and second arms for releasable attachment to the first and second members of the body joint, respectively. Essentially, that a gimbal assembly connects the first and second arms for their relative rotation in two perpendicular planes. Preferably, first and second potentiometers generate signals indicative of an angle between the first and second arms in each plane.

A miniaturized electronic module reads and processes signals from the potentiometers. It is essential, that the electronic module can be pre-programmed from a remote computer by a physician or a technician in order to pre-set an allowed range of motion in each plane of motion.

Preferably, a number of times when the signals from the potentiometers fall within the allowed range of motion and a number of times the allowed range of motion has been exceeded are stored in the electronic module.

Once the allowed range of motion has been exceeded, the electronic module generates an alarm signal.

All data are stored in the electronic module for a certain time period (24 hours to 48 hours, etc.), preferably, when the patient is out of the medical facility. On a regular basis, these stored data are down-loaded to the remote computer for further analysis. For this purpose, the patient does not need to come to the medical facility. He (or she) just has to use the interface (modem) to transmit the stored data to the remote computer, such that the data further are processed and/or analyzed. On the basis of the analysis, the physician or technician re-program the electronic module through the computer at the medical facility. Again, the presence of the patient is not needed at the medical facility, since the electronic module can be hooked to at any computer available for the patient and communicating with the computer at the medical facility.

Preferably, the re-programming includes re-adjustment of the allowed range of motion as a rehabilitation process is in progress.

The electronic module is accommodated within a miniature housing worn by a patient, such that the patient can go about his (or her) normal activities while being monitored by means of the joint monitor.

A program software in the electronic module measures resistor-capacitor (RC) time constant of each potentiometer in association with an auxiliary capacitance which is indicative of an angle between the first and second arms in a respective plane, and determines a resistive component of the RC time constant which is considered as the signal from each potentiometer and is further processed to obtain an angle corresponding to the resistive component and to determine whether the angle falls into the allowed range of motion.

For better results of the study, the allowed range of motion in each plane is divided into several angle areas (quadrants) of a particular interest for a physician or at least one area of motion of interest is predetermined within the allowed range of motion; and the software determines whether the angle falls into a certain quadrant.

The joint monitor allows a wide angle range for the first and second arms motion, ranging 0–250 angular degrees in one plane and 0–90 angular degrees in another plane. An angle resolution (or accuracy) in each plane does not exceed 1.5 angular degrees.

The gimbal assembly includes a gimbal body having cylindrical side walls and annular upper and bottom surfaces. Preferably, a shaft of the first potentiometer protrudes through the joint end of the first arm and is secured to the gimbal body, such that the shaft of the first potentiometer coincides with the central axis perpendicular to the upper and bottom annular surfaces of the gimbal body. The second arm, preferably, has a pair of spaced extensions at the joint end thereof, such that the gimbal body rotates between the extensions with an axis of rotation passing between the extensions through said cylindrical walls and parallel to said annular upper and bottom surfaces of the gimbal body. The shaft of the second potentiometer is secured to one of said spaced extensions and is secured to the gimbal body coinciding with said axis of rotation. The shell of each potentiometer is secured to a respective arm.

Once the first and second arms are releasably attached to the first and second body members of the body joint, the angle measured between the first and second arms in each plane corresponds to an angle between the first and second body members. Optionally, the angle can be measured between the arm and a reference line (for instance, a vertical or horizontal axis).

Viewing in another aspect, the present invention is a method for monitoring a body joint of a patient by the dual-plane joint monitor as described above.

According to the method, the body monitor is attached to the body joint, such that an angle between the arms corresponds to an angle between body joint members in each of the perpendicular planes of rotation. An allowed range of motion is preset in the electronic module from the remote computer. Then, the patient is free to leave the medical facility in order to perform physical activity (rehabilitational or routine) during a certain period of time (24 hours, 48 hours, etc.) during which the signals from the potentiometers are read, processed and stored within the electronic module.

After the period of time, determined by the physician or technician, the stored data are to be down-loaded from the electronic module to the remote computer (directly, or via interface or network, or saved onto a floppy disk to be further inserted in a disk drive of the personal computer (PC)

at the medical facility). This allows to avoid the patient to be at the medical facility often. The data transmitted to the remote computer are analyzed and/or processed, and the result of the analysis may be used for further re-programming (or re-adjustment) of the electronic module. The technician or physician can re-program the electronic module (which is out of the medical facility) directly from the remote computer in the medical facility, or, as discussed above, via a modem, network, or by sending a floppy disk with necessary controlling data to the patient's address.

Each time, when the motion of the patient exceeds the allowed range of motion in either plane, the alarm sounds (or flashes).

These and other objects of the present invention will become apparent from a reading of the following specification taken in conjunction with the enclosed drawings.

DESCRIPTION

Referring to FIGS. 1–10, a dual-plane joint monitor 10 is removably applied to a body joint 11 of a patient 12 at a medical facility. A physician, or technician (not shown), pre-programs an electronic module 13 of the joint monitor 10 via a computer 14 at the medical facility (further referred to as a remote computer). In course of the pre-programming, the physician sets up an allowed range of motion for the patient 12, such that when the patient 12 performs his (or her) physical activities, a logic 15 in the electronic module 13 reads signals indicative of those physical activities and analyses them to make sure that the allowed range of motion is not exceeded. In the event that the allowed range of motion is exceeded, the electronic module 13 generates an alarm signal for the patient 12.

Figure 1:
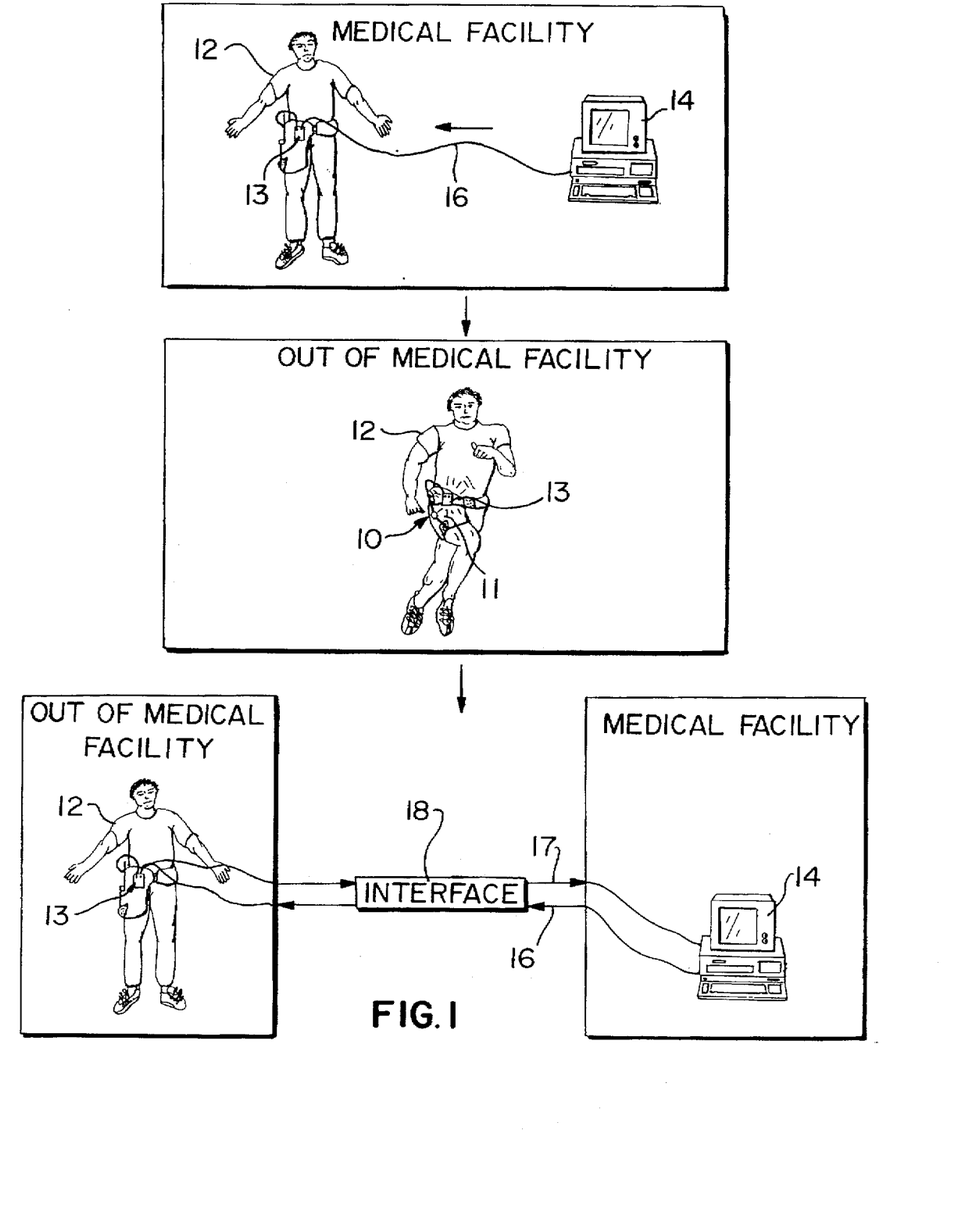
FIG. 1 shows, somewhat schematically, the sequence of operations for practicing the method of the present invention.

As best shown in FIG. 1, the electronic module 13 is pre-programmed via a cable 16 connecting the logic 15 of the electronic module 13 to a parallel port of the remote computer 14 at the medical facility.

Optionally, pre-programming and/or re-programming can be done if the patient 12 is out of the medical facility through a parallel port of any computer (which is part of the remote computer 14 network) or the data and software for pre-programming and re-programming can be saved to a floppy disk or a compact disk and loaded into the logic 15 of the electronic module 13 from any PC available for the patient 12. Once the joint monitor 10 has been put onto the patient 12, and the pre-programming of the electronic module 13 has been done, the patient 12 can perform his (or her) rehabilitation physical activity or his (or her) normal daily activity out of the medical facility.

Data of the patient's motion are collected, processed and stored within the electronic module 13 during a certain period of time determined by the physician (typically, 24 to 48 hours, depending on activity), and then the stored data are to be downloaded to the remote computer 14 which is located at the medical facility.

Again, similar to the programming, downloading can be done directly at the medical facility through a serial cable 17, or the data can be transmitted to the remote computer 14 through an interface 18 of the electronic module 13, through the network, or by means of downloading the data to a floppy disk (compact disk) and sending it to the medical facility for further loading to the remote computer 14 for further processing.

The remote computer 14 further processes and/or analyses the data from the electronic module 13, and, on the basis of the results of analysis, the physician may re-program the electronic module 13 to alter the allowed range of motion or to exchange the area of motion of interest. Similar to the pre-programming step, the patient does not need to come to the medical facility for re-programming. The command and data will be sent to the electronic module 13 on the patient 12 through any software and data transmitting media (network, diskettes, interface, or the like). The patient 12 will only need to connect the electronic module 13 to any available to him (or her) computer via the parallel cable 16 for the re-programming.

For the sake of simplicity, the joint monitor 10 will be further described for application to a hip joint, however the principles of the present invention are equally applicable to a monitor for any body joint of the human body.

As best shown in FIGS. 2–9, the joint monitor 10 includes a lower arm 19 and an upper arm 20 joined by a gimbal assembly 21 for their relative rotation in two perpendicular planes. A pair of potentiometers, 22 and 23, are secured to the lower and upper arms 19, 20 at the place of their connection for measuring rotation angle between the arms 19, 20 in each of the perpendicular planes of rotation. The electronic module 13 reads signals from the potentiometers 22, 23 and processes them according to the inherent software program.

Figure 2:
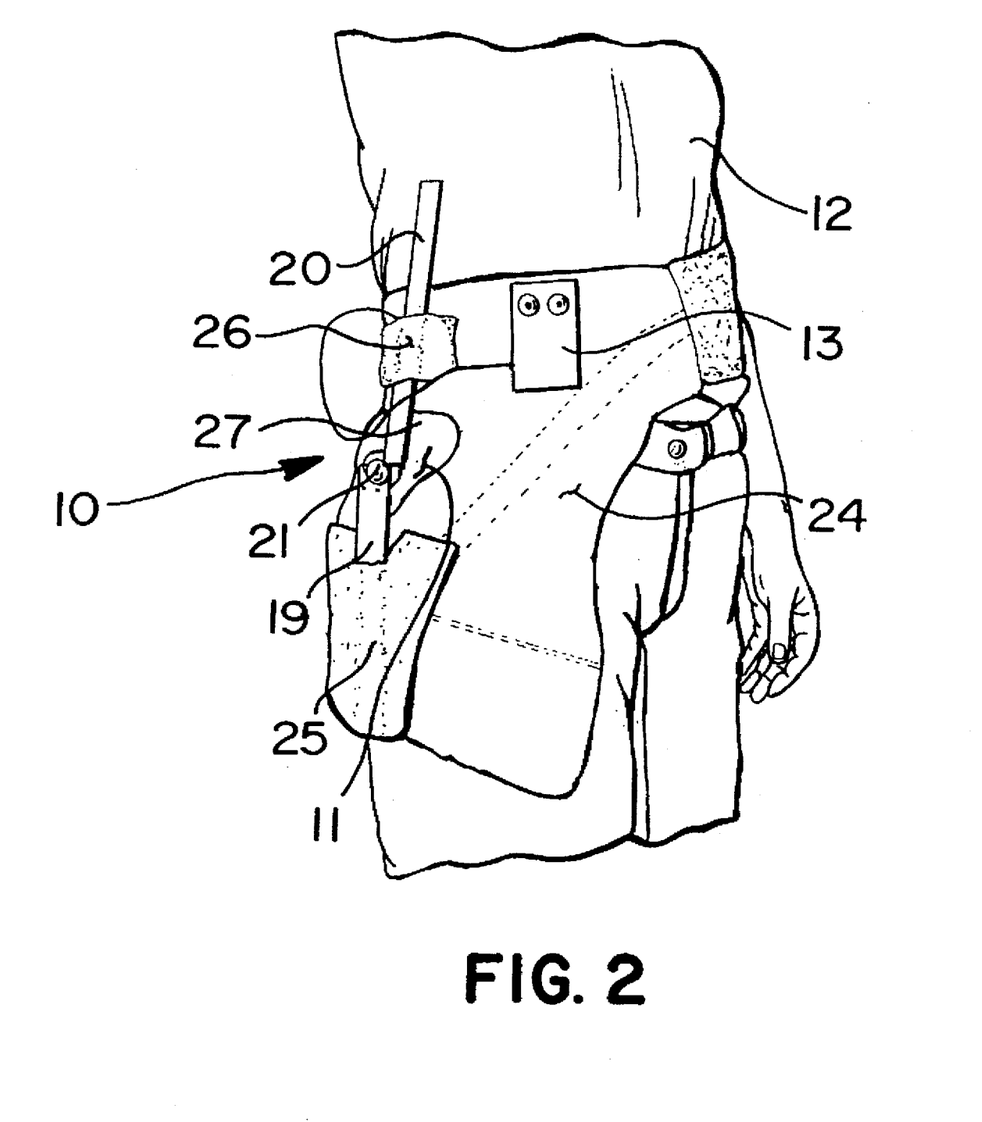
FIG. 2 is a pictorial view of a patient wearing the joint monitor of the present invention.
Figure 3:
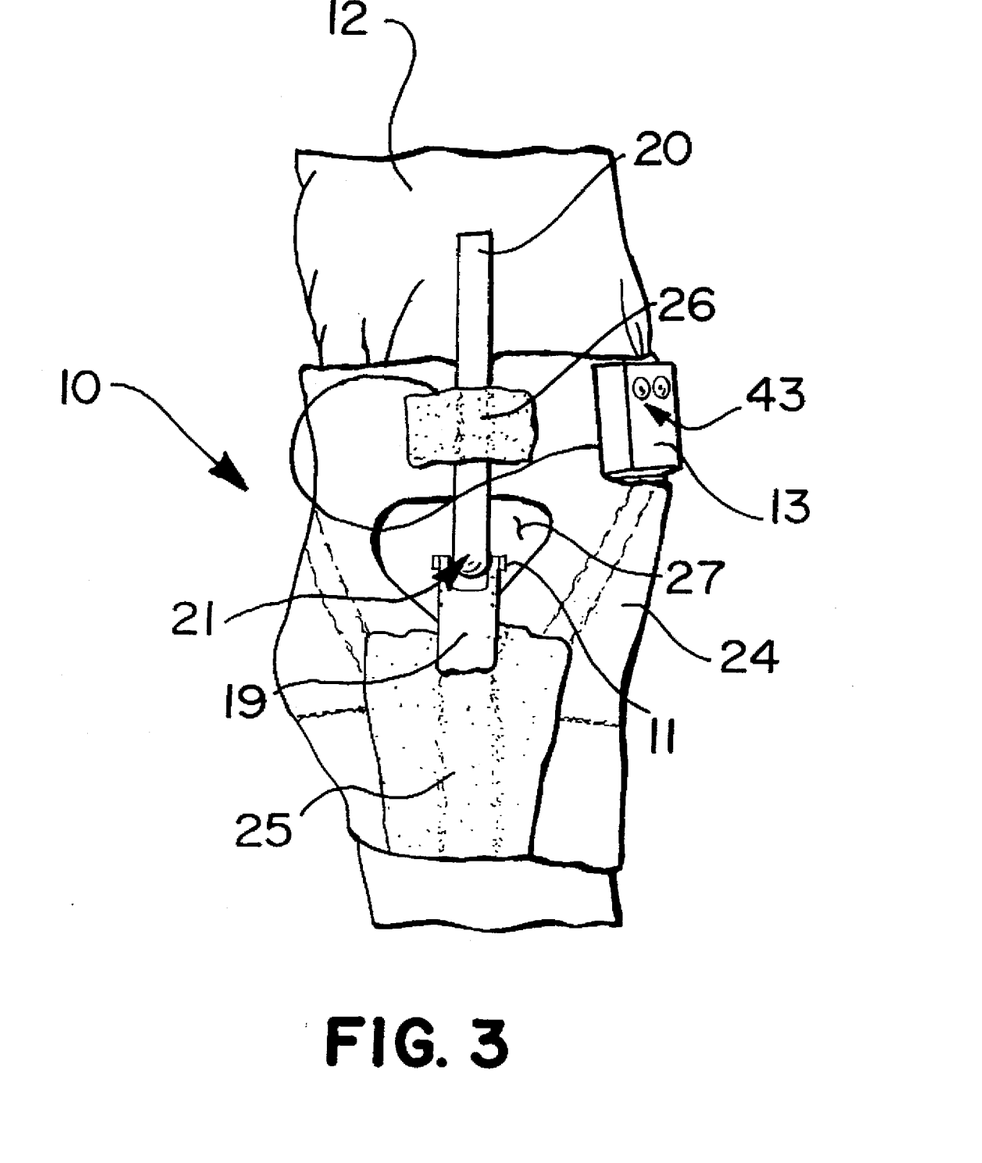
FIG. 3 is a side pictorial view of the patient of FIG. 2.
Figure 4:
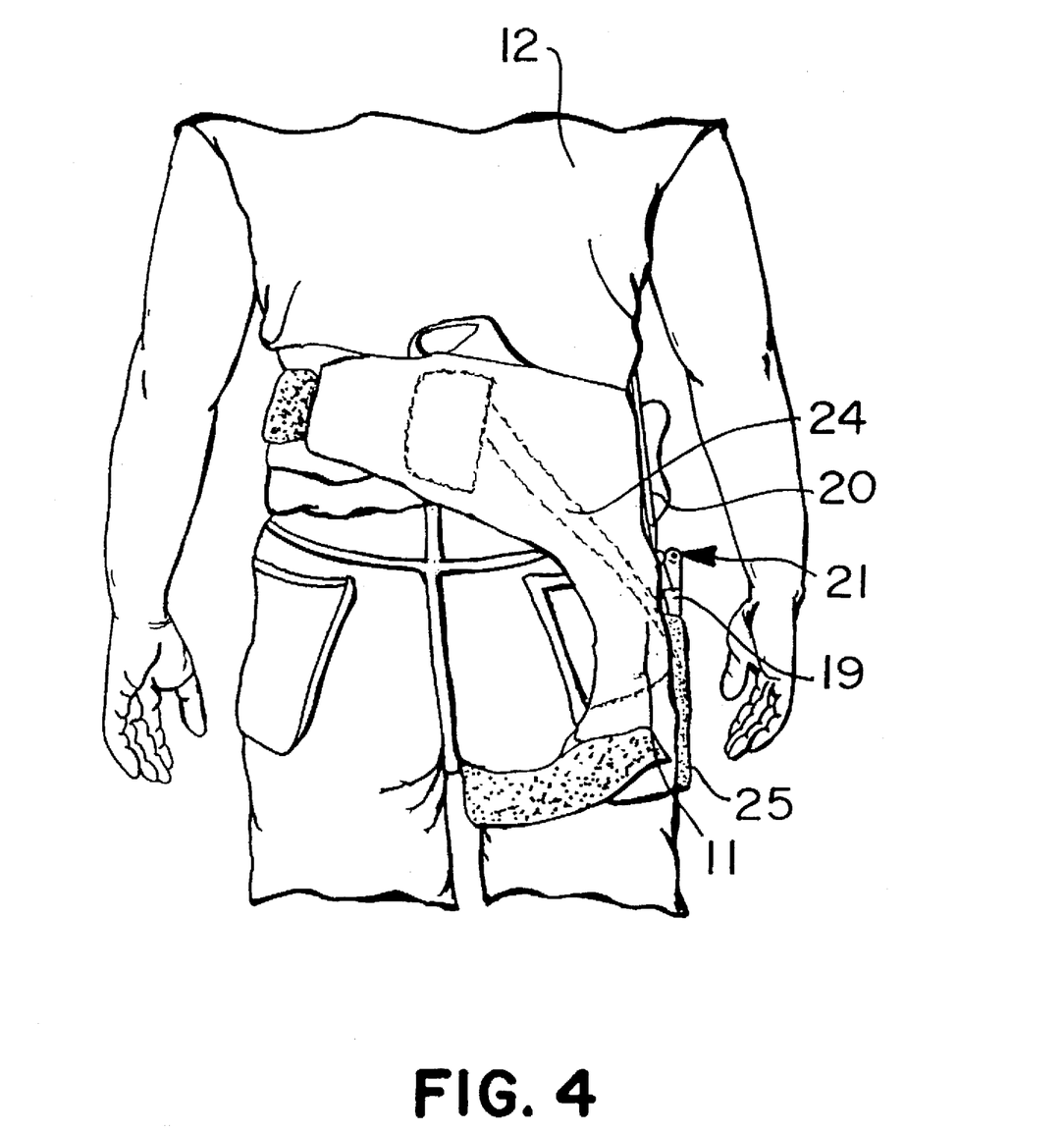
FIG. 4 is a back pictorial view of the patient of FIGS. 2 and 3.

The lower arm 19 is releasably attached to the thigh of the patient 12, while the upper arm 20 is releasably attached to the hip, such that to monitor the hip joint. Both arms 19 and 20 can be strapped to the body joint member by plastic loops, however, preferably, an elastic adjustable neopream support 24 (as best shown in FIGS. 2–4) precisely following the contours of the body and maintaining the joint monitor 10 in place (as it was put on by the physician at the medical facility), and providing that the joint monitor 10 will not be deviated from the place during a physical activity, is to be used.

The neopream support 24 can be a standard one, modified, however, for a secure and precise attachment of the arms 19, 20 and the electronic module 13 thereto. As best shown in FIGS. 2–4, the neopream support 24 is improved by a lower "pocket" 28 fastening the lower arm 19 to the support 24 below the hip joint. An upper securing means 26 fastens the upper arm 20 to an upper part of the support 24 above the hip joint. It will be appreciated by those skilled in the art, that it can be a bar adhered or sewed on the neopream support 24, or any of the means maintaining the upper arm 20 attached to the support 24 in pre-selected position. An opening 27 in the neopream support 24 is placed against the hip joint, such that the gimbal assembly 21 is located exactly on the imaginary axis of rotation of the hip joint.

The electronic module 13 is secured to the neopream support 24 in a convenient place such that the patient 12 can go about his (or her) daily activities with no inconveniences.

When the patient moves, either performing normal or injury recovering motions, the hip and the thigh are rotated relative to each other in two perpendicular planes (excursion in one plane, and adduction in another plane), and the lower and the upper arms 19, 20 exactly mimic the motions of the hip and the thigh.

As best shown in FIGS. 5–9, the upper arm 20 is a flat bar made of a light yet strong material having a hole (not shown) on its joint end 28. The lower arm 19 is also a flat bar made of the same material as the arm 20 and has a pair of spaced extensions 29, 30 secured to a joint end 31 of the lower arm 19. The extensions 29, 30 are located substantially perpendicular to a flat surface 32 of the lower arm 19, and the extension 29 has a hole 32 in precise registration with the hole 33 on the extension 30.

Figure 5:
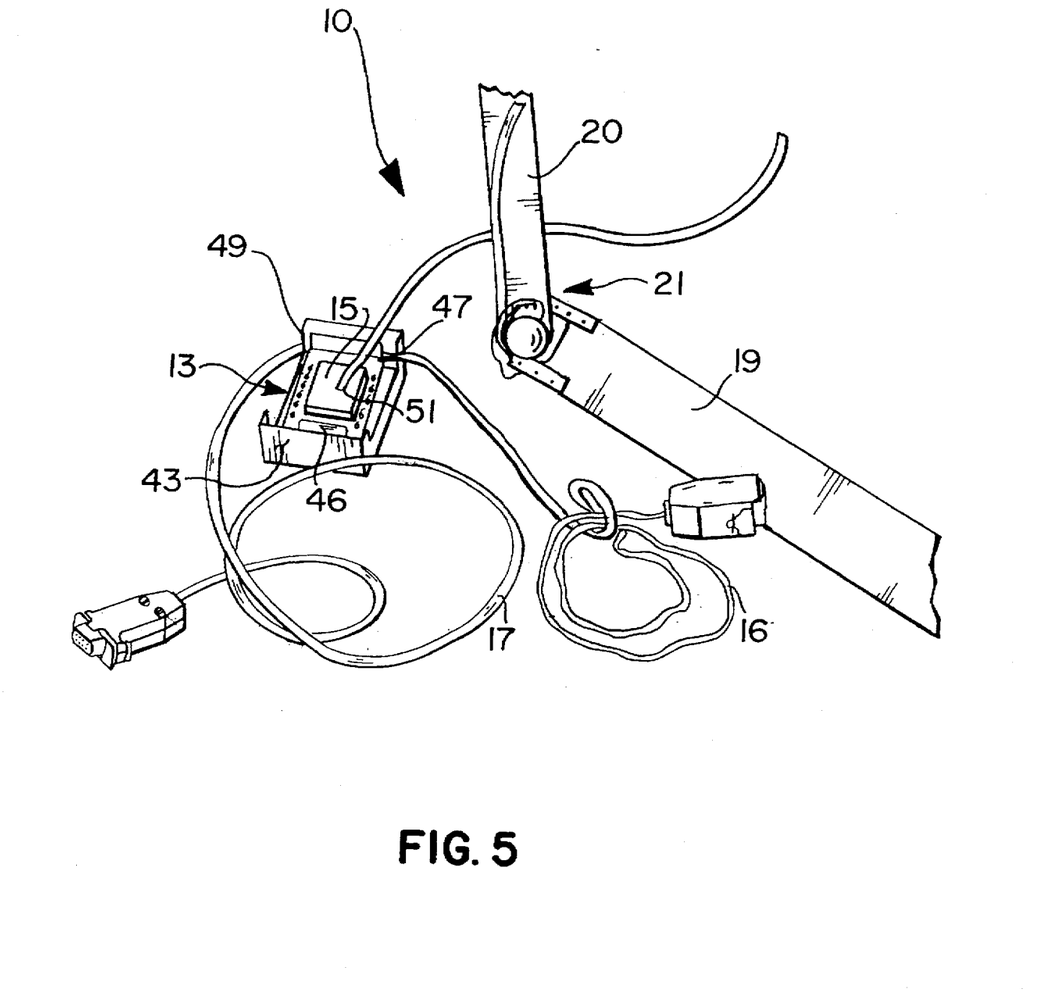
FIG. 5 is a perspective view of the joint monitor of the present invention with down-loading serial cable and program parallel cable coupled to the electronic module.
Figure 6:
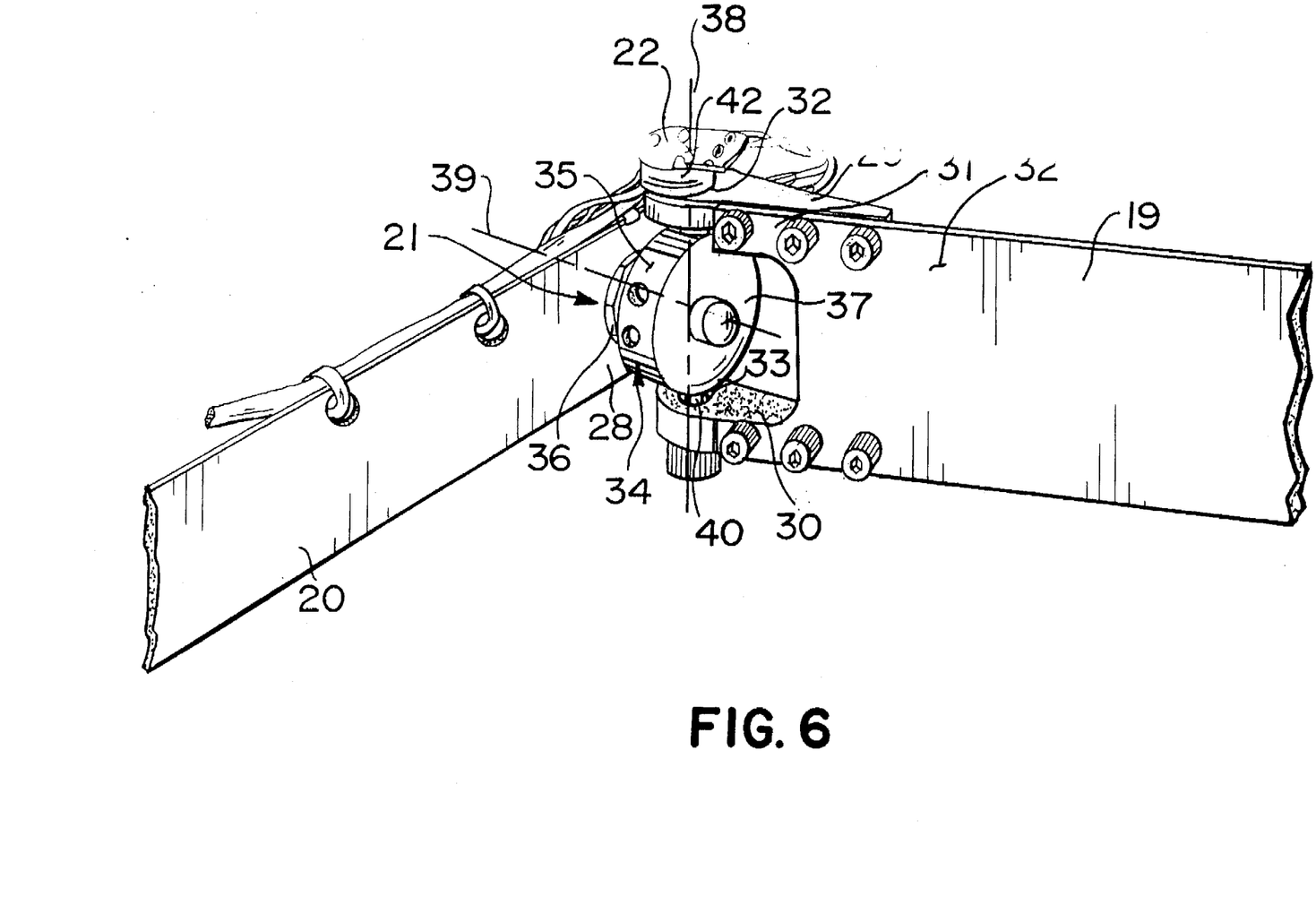
FIG. 6 is another perspective view of the joint monitor of the present invention showing, on enlarged scale, the gimbal assembly and one of the potentiometers.
Figure 7:
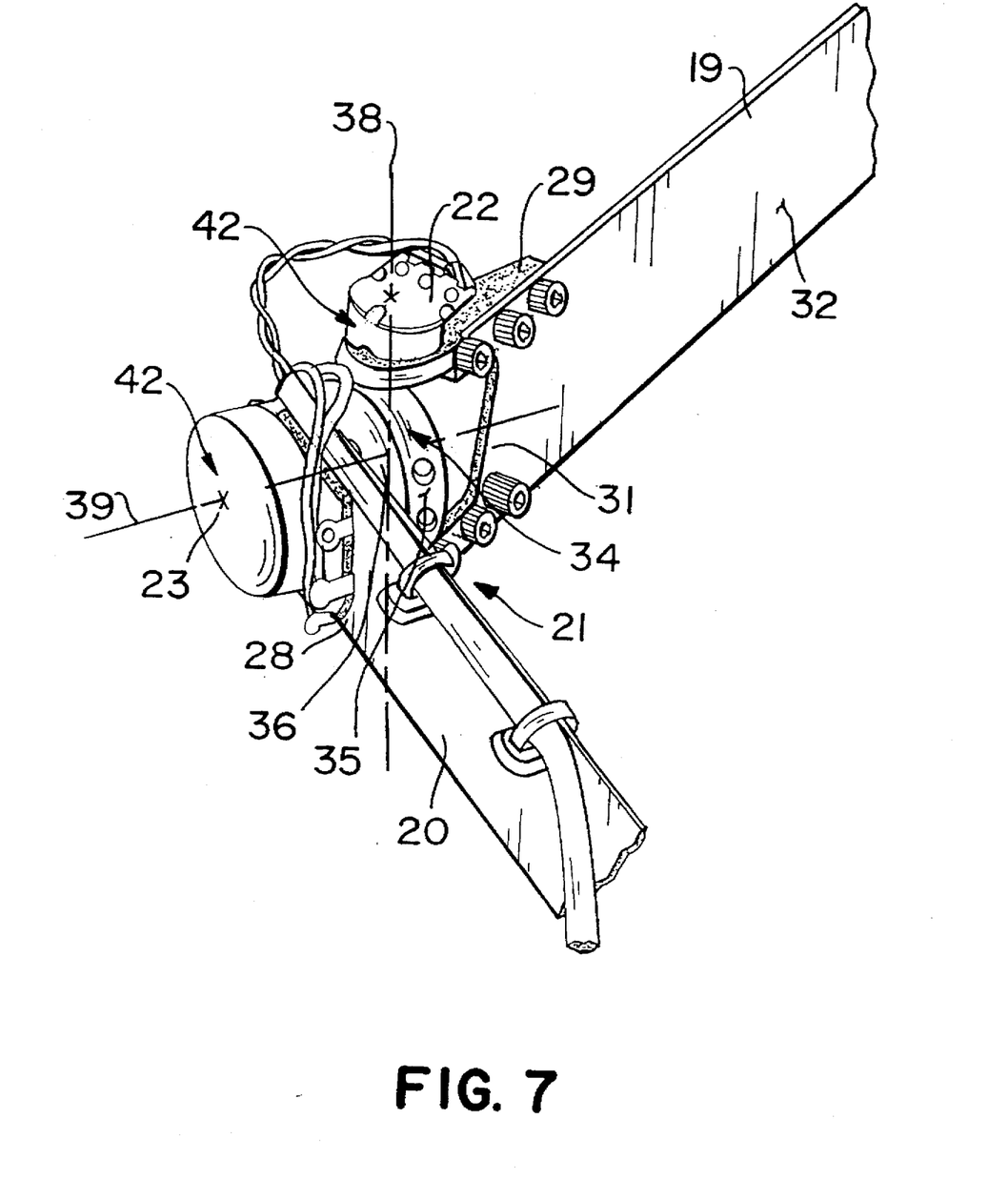
FIG. 7 is yet another perspective view of the joint monitor of FIG. 6 clearly showing both potentiometers and their mutual disposition.

The joint end 31 of the lower arm 19 is shaped in such a way that to allow a gimbal body 34 of the gimbal assembly 21 to freely rotate between the extensions 29 and 30. The gimbal body 34 has cylindrical side walls 35 and annular upper and bottom surfaces 36, 37, respectively. The gimbal body 34 has two perpendicular rotational axes 38, 39. The axis 38 passes through the holes 33 at the joint end 31 of the lower arm 19, and the axis 39 passes through the hole (not shown) at the joint end 28 of the upper arm 20.

The potentiometer 22 is secured to the lower arm 19 and to the gimbal body 34, such that a shaft 40 thereof passes through the hole 33 of the extension 29 and into the cylindrical side wall 35 of the gimbal body 34 and coincides with the rotation axis 28. The potentiometer 23 is secured to the upper arm 20 and to the gimbal body 34, such that the shaft (not shown) of the potentiometer 23 passes through the hole at the joint end 28 of the upper arm 20 and into the gimbal body 34 centrally and perpendicularly to the annular upper and bottom surfaces 36, 37 coinciding with the rotational axis 39. A circular shell 42 of the potentiometer 22 rotates around the gimbal body 34 along with the lower arm 19, while a circular shell 42 of the potentiometer 23 rotates around the gimbal body 34 along with the upper arm 20. It will be appreciated by those skilled in the art that each of the shafts of the potentiometers 22 and 23 serves as one bearing at a respective axis, while the second bearing is implemented by a sleeve-type bearing.

Opposite to the potentiometer 22, the gimbal body 34 is provided with a bearing passing through the hole 33 in the extension 30 for rotation around the axis 38.

The potentiometers 22, 23 are commercially available potentiometers and each comprises a resistance element (not shown) embodied in a circular shell 42 and a sliding contact to vary the effective resistance of the potentiometer. The effective resistance vary in accordance with the position of the shaft with respect to the outer shelf 42, and since the shaft is secured to the gimbal body 34, and the outer shelf 42 is secured to the respective lower or upper arm 19, 20, the effective resistance of the potentiometer will vary according to the angle formed between the gimbal body 34 and the respective lower or upper arm 19, 20. Since the gimbal body 34 is immovably secured to the hip joint of the patient 12, it is easy to establish a certain reference position in both perpendicular planes such that the effective resistance of the potentiometers 22, 23 will be indicative of the angular movement of the lower and upper arms 19, 20 in these perpendicular planes. Therefore, if the lower and the upper arms 19, 20 are aligned with the limbs of the body joint, the effective resistance of the potentiometers 22, 23 is a function of angular motion of the limbs of the body joint (either relative to each other or relative to the reference position).

Figure 10:
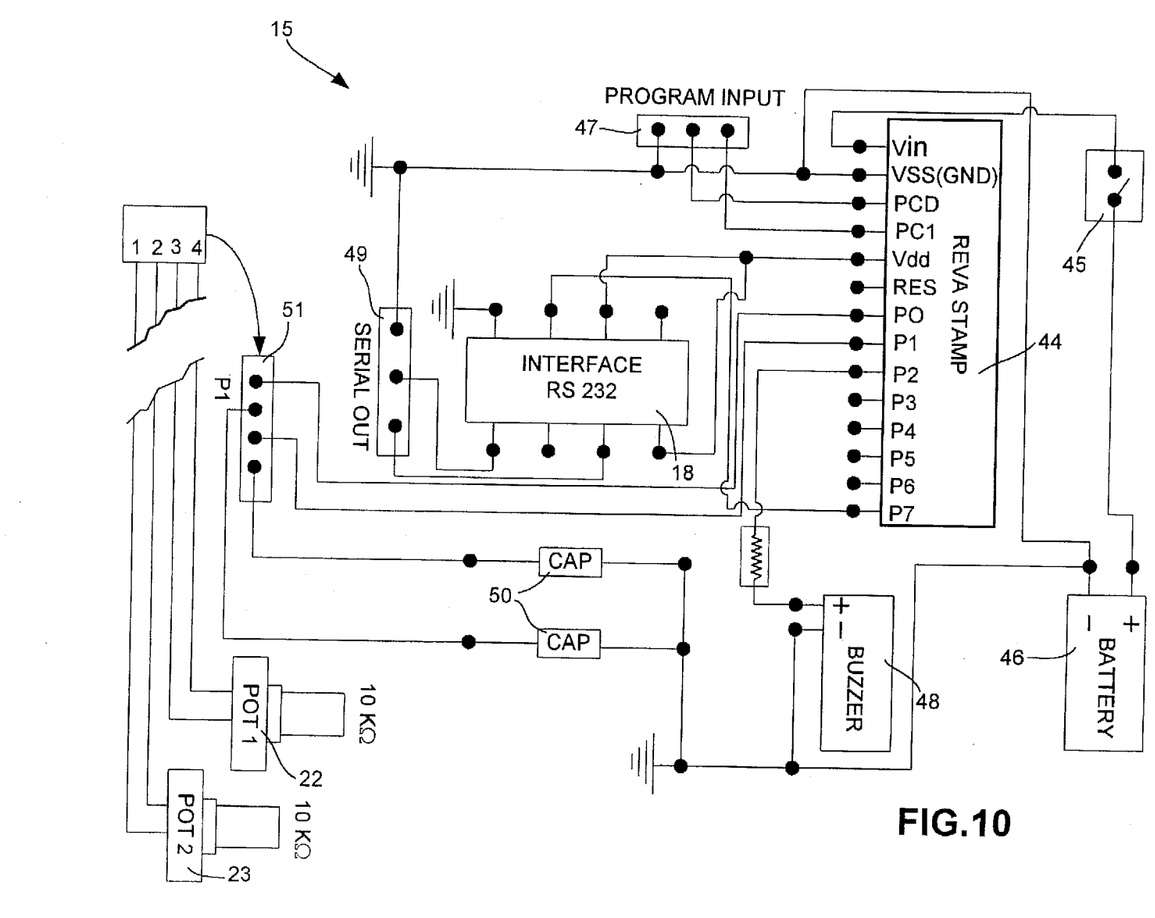
FIG. 10 is a functional block diagram of the joint monitor of the present invention shown in FIGS. 1–9.

As best shown in FIG. 10, a pair of capacitors "CAP" is provided within the electronic module 13. In order to determine the angular position of the limb of the body joint, the electronic module 13 is programmed to measure resistor/capacitor time constant (R/C time) of each potentiometer 22, 23 in association with a respective capacitor and to determine the effective resistance value in the R/C time.

Figure 8:
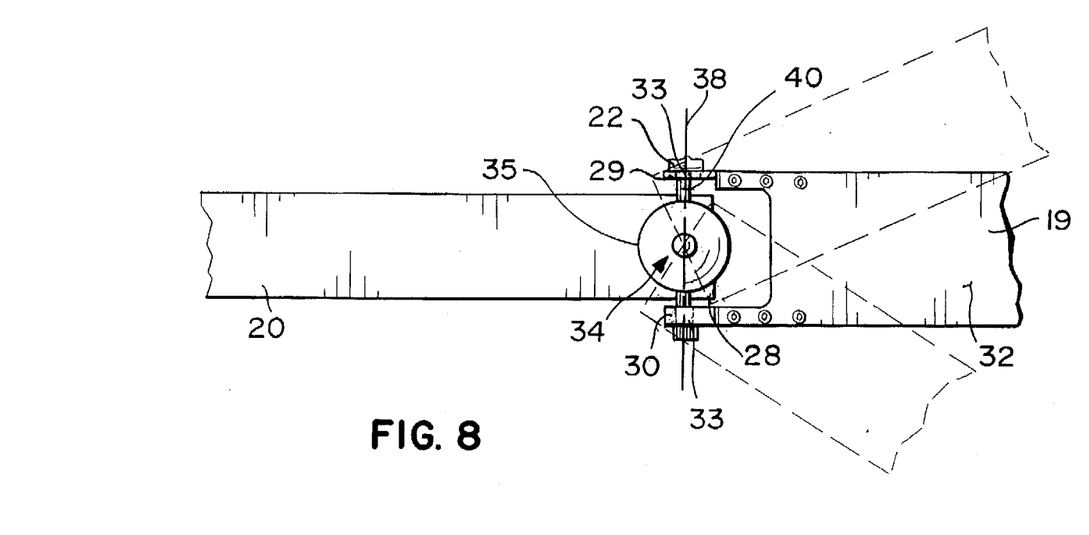
FIGS. 8 and 9 show somewhat schematically relative rotation of the arms in two perpendicular planes.
Figure 9:
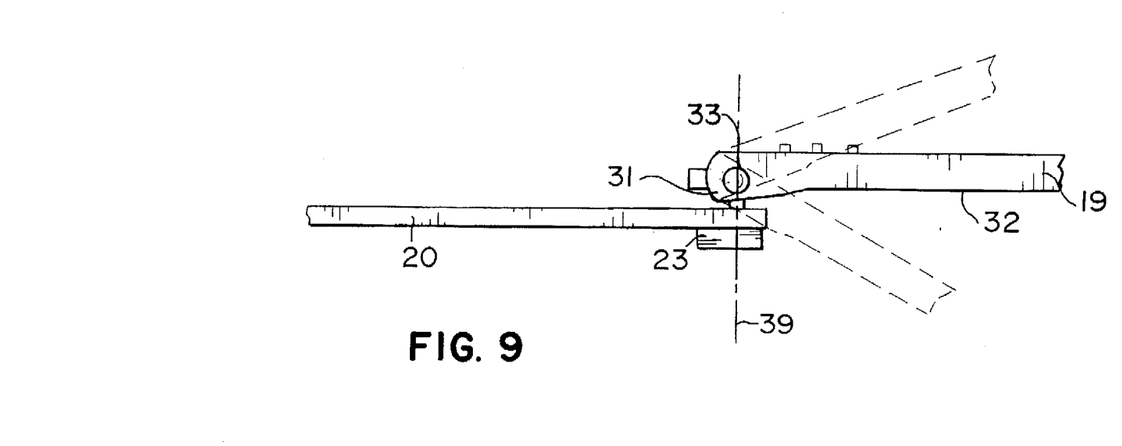

As it is best shown in FIGS. 8 and 9, an angular interval of relative rotation of the lower and upper arms 19 and 20, in one plane is 0–250 angular degrees and in another plane is 0–90 angular degrees. An angle resolution (or accuracy) in both planes does not exceed 1.5 angle degrees.

The electronic module 13 is accommodated in a miniature housing 43 for convenience and is carried by the patient, preferably, on the neopream support 24.

As best shown in FIG. 10, the electronic module 13 includes an electrically erasable programmable read-only memory (EEPROM) processor 44 (manufactured by Parallax) also referred to as the Basic Stamp® (BSI-IC) powered through the switch 45 from a battery 46. The processor 44 is programmed via the port 47 (PROGRAM IN) through which the allowed range of motion and areas of particular interest are loaded thereinto from the remote computer 14 at the medical facility or from any computer available to the patient 12 (as discussed above). The cable 16 for loading a pre-programming and re-programming information into the processor 44, is provided in the set with the joint monitor 10, and, when needed, is coupled between the port 47 and a parallel port of the remote computer 14 (or any other available PC out of the medical facility). The Basic Stamp® 44 measures the R/C time constant of each potentiometer 22, 23 in association with the capacitance CAP 50. For this purpose (as best shown in FIG. 10), two capacitors 50 of known value are connected to the input 51 of the electronic module 13. When both potentiometers 22, 23 are connected to the signal receiving input 51 of the electronic module 13, R/C time constant of each of the potentiometers in association with a respective one of the capacitors 50, is measured. Each R/C time constant is considered as the signal from each potentiometer 22, 23 and is supplied to P0 and P1 ports of the processor 44 for being further processed. Since the value of each capacitor 50 is known, the processor determines a resistive component of the R/C time constant of each potentiometer, and further determines an angle corresponding to said resistive component equal to the effective resistance of the potentiometer. Further, the processor 44 determines whether the determined angle falls into the predetermined allowed range of motion or into the predetermined area of interest, or in a certain quadrant predetermined for the processor through the program INPUT port 47. The processor 44 stores in the memory the data of how often (or how many times) the motion of the patient falls within the allowed range, or the area of interest, and how often the predetermined range of motion has been excluded.

It will be appreciated by those skilled in the art from the above discussion, that the motions of the patient is monitored continuously, and that the R/C time constant supplied to the processor 44, is indicative of the respective potentiometer position. This R/C time constant is measured each time the potentiometer position changes, and is then used to determine whether the potentiometer position is in or out of the allowed range of motion or the area of particular interest.

If the allowed range of motion is exceeded, the buzzer 48 is activated. The buzzer 48 can be any alarming device employed in the art, and can generate warning sound, siren, or light.

Figure 11:
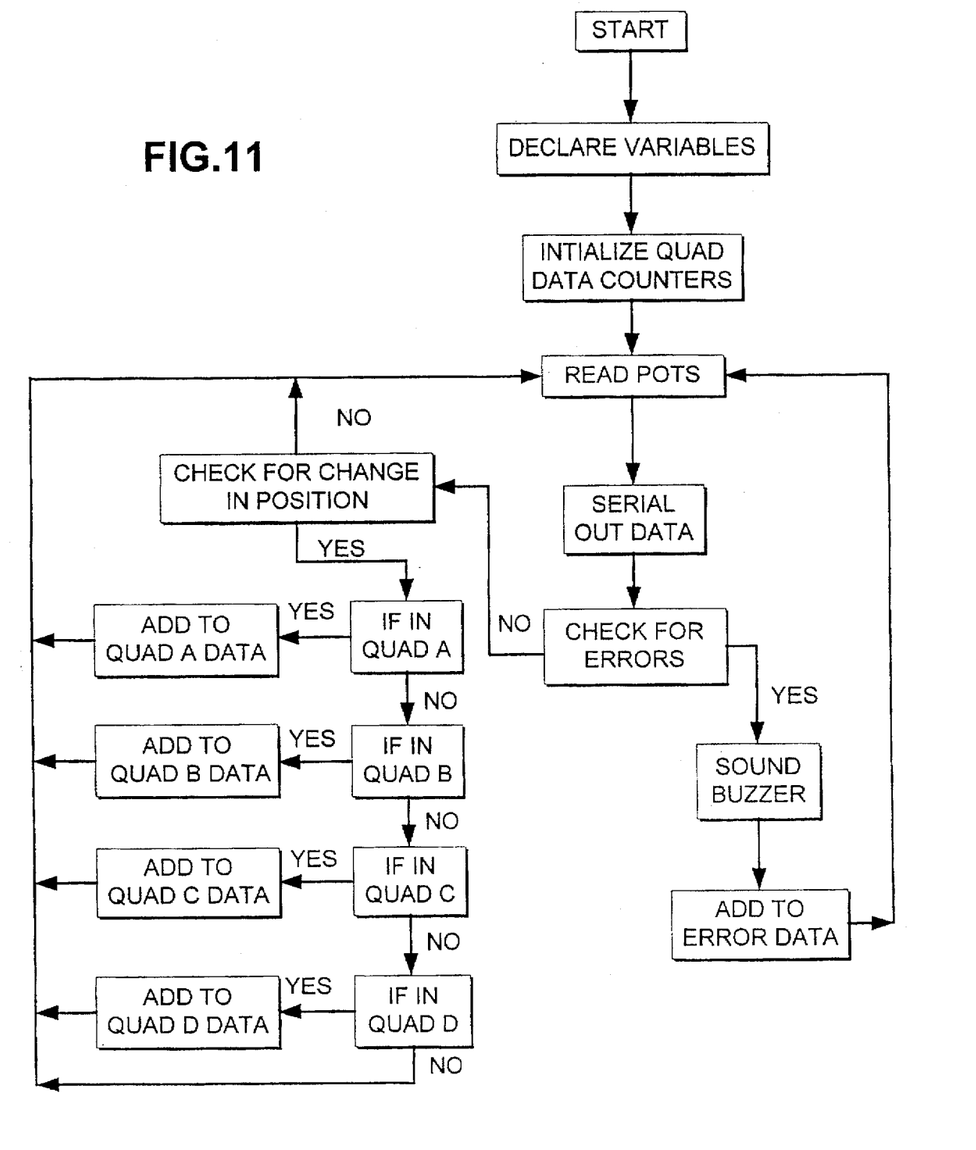
FIG. 11 is a functional flowchart of a program software operating the joint monitor according to the principles of the present invention. (Appendix A is a program listing of the program of FIG. 11.)

As best shown in FIG. 11, and in Appendix A, four quadrants (Quad A, Quad B, Quad C, and Quad D) have been chosen in this particular arrangement, however any other distribution of areas of interest is possible and is perfectly applicable within the scope of the present invention. When the alarming situation occurs, the Basic Stamp® records the position in the form of counts in the particular range of motion predetermined by the physician by programming the Basic Stamp®. This data is stored and then can be transmitted through the interface (RS 232) 18 into the remote computer 14 for evaluation of motion during a certain period of time (24 to 48 hours, depending on activity prescribed by the physician).

The Basic Stamp® also registers a number of times the position in the selected particular range occurs, and number of times the total allowed range of motion has been exceeded. These data are also stored in the processor 44 for being downloaded to the remote computer 14 through the interface 18. For this purpose, the serial cable 17 is provided in the set with the joint monitor 10 for being connected between the serial port 49 of the processor 44 and the remote computer 14 (or any available PC, as discussed above). The data are to be downloaded on a regular basis in order not to overload the data register of the processor 44.

As best shown in FIGS. 11 and 12, the software for Basic Stamp® processor 44 which is written in P-Basic (Basic Stamp® language), sends power to the potentiometers 22, 23 and measures the R/C time, which is then analyzed to determine if limits of the allowable range have been exceeded, and to sound the buzzer once this situation occurred. Positions falling within the smaller ranges of motion (discussed above) are recorded in counters which will form a histogram of activity when downloaded into the remote computer 14. The ranges are determined at time of pre-programming and depend on the area of motion of interest. This can only be altered by means of re-programming the Basic Stamp® processor 44 via a parallel port on any available computer or can be saved to a diskette and loaded into the processor 44 via a cable from any computer.

The joint monitor 10 can also be used while connected to a computer for higher resolution in motion monitoring.

The joint monitor 10 of the present invention has multiple applications, with the following three primary ones:

To monitor a patient's hip precautions after arthoplastic surgery (hemi or total) of the hip. This includes a biofeedback mechanism notifying the patient that he (or she) just violated the motion precautions, such as flexion or adduction past neutral. This facilitates the patient training process as well as compliance. The device can be set to alarm at any preset angle.

to monitor a patient's compliance and progression of knee mobility, mainly flexion-extension, after total knee replacement.

The device collects data that would allow the physician to predict when the patient falls off the expected progression curve or is progressing faster than usual. This has implications for quantifying length of physical therapy to be needed. Also, any laxity in the varus or valgus plane can be monitored.

To be used as a research tool: to study relationship between a body joint motion, quantitatively, and outcome after arthoplastic procedures; to study the relationship between joint motion in-vivo and pathologic processes such as low back pain, arthritic degeneration, or risk of injury; to study the effect of various exercises or strengthening programs on in-vivo joint motion ranges during normal or sport (stressed) activities.

Besides the discussed above applications, the monitor of the present invention can monitor preoperative range of motion in a patient's normal environment, can access different joint motions experienced during sporting activities (such as, for instance, golf); can assist in training of organisms to perform better, to run faster, to pursue a desired task with more precaution using the device's biofeedback capabilities.

Obviously, many modifications may be made without departing from the basic spirit of the present invention. Accordingly, it will be appreciated by those skilled in the art that within the scope of the appended claims, the invention may be practiced other than has been specifically described herein.

APPENDIX A
(pages 1–3)

```
'POT HIP MONITOR 5-3-96
SYMBOL SWING=B1
SYMBOL CROSS=B2
SYMBOL ERROR=B3
SYMBOL ABD=B4
SYMBOL BBD=B5
SYMBOL CBD=B6
SYMBOL DBD=B7
SYMBOL CHANA=B8
SYMBOL CHANB=B9
SYMBOL CHANGE=B10
SYMBOL CHANC=B11
SYMBOL CHAND=B12
CHANA=0
CHANB=0
CHANC=0
CHAND=0
CHANGE=0
STARTA:
'READ POTS
    POT 0,126,CROSS
    POT 1,134, SWING
    PIN1=0
Serialout (ABD,BBD,CBD,DBD,ERROR)
CHECK ERROR
    IF B1<23 THEN FAIL
    IF B1>220 THEN FAIL
    IF B2>138 THEN FAIL
    IF B2<118 THEN FAIL
    LOW 2
    GOTO HIST
    FAIL:HIGH 2
    IF CHANGE=0 THEN ERR
    GOTO STARTA
    ERR:CNANGE=1
    ERROR=ERROR+1
    CHANA=0
    CHANB=0
    CHANC=0
    CHAND=0
    GOTO STARTA
```

-continued

APPENDIX A
(pages 1-3)

```
'HISTOGRAM DATA
HIST:
        CHANGE=0
        IF B1<43 OR B1>86 THEN A
        CHANB=0
        CHANC=0
        CHAND=0
        IFCHANA=1 THEN A1
           ABD=ABD+1
              CHANA=1
        GOTO STARTA
        A1:GOTO STARTA
A:      IF B1<86 OR B1>128 THEN B
        CHANA=0
        CHANC=0
        CHAND=0
        IFCHANB=1 THEN E1
           BBD=BBD+1
        CHANB=1
        GOTO STARTA
           E1: GOTO STARTA
B:      IF B1<128 OR B1>171 THEN C
        CHANA=0
        CHANB=0
        CHAND=0
        IF CHANC=1 THEN C1
           CBD=CBD+1
        CHANC=1
        GOTO STARTA
           C1: GOTO STARTA
C:      IF B1<171 OR B1>213 THEN D
        CHANA=0
        CHANB=0
        CHANC=0
        IF CHAND=1 THEN D
           DBD=DBD+1
        CHAND=1
        GOTO STARTA
D:      GOTO STARTA
```

We claim:

1. A dual-plane joint monitor for a body joint of first and second body members, the dual-plane joint monitor comprising:

first and second arms for releasable attachment to the first and second body members, respectively, each arm having a respective joint end;

a gimbal assembly connecting the joint ends of the first and second arms for their relative rotation in two perpendicular planes;

first and second potentiometers, each at said joint end of a respective one of the first and second arms, for generating a signal indicative of an angular motion of the first and second arms in each of said two perpendicular planes; and an electronic module receiving and processing the signals from said first and second potentiometers, and including means for receiving, from a remote computer, data establishing an allowed range of motion in each said plane, and means for determining whether said allowed range of motion in each plane has been exceeded.

2. The joint monitor of claim 1, wherein the electronic module further includes means for storing a number of times when the signals from the first and second potentiometers fall within the respective allowed range of motion.

3. The joint monitor of claim 1, wherein the electronic module further includes means for storing a number of times the allowed range of motion in each plane has been exceeded.

4. The joint monitor of claim 1, wherein the electronic module further includes means generating alarm signal once the allowed range of motion has been exceeded.

5. The joint monitor of claim 1, wherein the allowed range of motion is adjusted from the remote computer according to a required schedule.

6. The joint monitor of claim 1, wherein the electronic module further includes means for storing, in a required format, data corresponding to the processed signals from the first and second potentiometers.

7. The joint monitor of claim 6, wherein said data are stored for a pre-selected time period.

8. The joint monitor of claim 6, further including means for down-loading, said data corresponding to the processed signals, to the remote computer for further analysis.

9. The joint monitor of claim 8, wherein said data are down-loaded with pre-selected time intervals.

10. The joint monitor of claim 1, wherein the electronic module is accommodated within a miniature housing worn by a patient, such that the patient can go about his (her) normal activities while being monitored with the joint monitor.

11. The joint monitor of claim 1, wherein the electronic module further includes a portable power source.

12. The joint monitor of claim 1, wherein the electronic module further includes two capacitors, each associated with a respective one of said first and second potentiometers, wherein a program software within the electronic module measures resistor-capacitor (R/C) time constant of each of said first and second potentiometers in association with a respective one of said capacitors, said R/C time constant being considered as the signal from said respective potentiometer, and further determines a resistive component of said R/C time constant, the resistive components being indicative of an angular motion of the first and second arms in a respective plane.

13. The joint monitor of claim 1, wherein an angle interval of relative rotation of the first and second arms in one plane is 0–250 angle degrees and in another plane is 0–90 angle degrees.

14. The joint monitor of claim 1, wherein an angle resolution in each plane does not exceed 1.5 angle degrees.

15. The joint monitor of claim 1, wherein the gimbal assembly includes a gimbal body having cylindrical side walls and annular upper and bottom surfaces, wherein each of the first and second potentiometers has a respective shaft, wherein the shaft of the first potentiometer protrudes through the joint end of the first arm and is secured to the gimbal body, such that said shaft of the first potentiometer coincides with the central axis perpendicular to said upper and bottom annular surfaces of the gimbal body, wherein the second arm includes a pair of spaced extensions at the joint end thereof, wherein the gimbal body is rotatably secured between said spaced extensions with an axis of rotation passing through said cylindrical walls parallel to said annular upper and bottom surfaces of the gimbal body, and wherein the shaft of the second potentiometer protrudes through one of said spaced extensions and is secured to the gimbal body coinciding with said axis of rotation.

16. The joint monitor of claim 15, wherein the gimbal body is releasably attached to the monitored body joint while the first and second arms are releasably attached to the first and second body members, respectively, such that the angular motion of the first and second arms in each plane corresponds to an angular motion of the first and second body members.

17. In a joint monitor provided with an electronic module for monitoring joint movement, the joint monitor including a pair of arms and further including at least one sensing element for generating a signal indicative of a relative angular motion between the arms, the improvement which comprises a gimbal assembly in the joint monitor to allow for monitoring of joint movement in two directions.

* * * * *